United States Patent [19]

Nash et al.

[11] 4,292,965
[45] Oct. 6, 1981

[54] INTRAVAGINAL RING

[75] Inventors: Harold A. Nash, Harrington Park, N.J.; Daniel R. Mishell, Jr., Palos Verdes Estates, Calif.

[73] Assignee: The Population Council, Inc., New York, N.Y.

[21] Appl. No.: 974,490

[22] Filed: Dec. 29, 1978

[51] Int. Cl.³ .............................................. A61M 7/00
[52] U.S. Cl. .................................. 128/260; 128/127; 424/22; 427/2; 427/413
[58] Field of Search ............... 128/127, 130, 172, 260, 128/261, 271; 424/16, 19, 22; 427/2, 430 R, 402, 413, 434 R, 434 D, 434 E

[56] References Cited

U.S. PATENT DOCUMENTS

| 3,545,439 | 12/1970 | Duncan | 128/260 |
|---|---|---|---|
| 3,832,252 | 8/1974 | Higuchi et al. | 128/260 |
| 3,920,805 | 11/1975 | Roseman | 128/260 |
| 4,012,496 | 3/1977 | Schopflin et al. | 128/260 |
| 4,012,497 | 3/1977 | Schopflin et al. | 128/260 |
| 4,096,239 | 6/1978 | Katz et al. | 128/260 |
| 4,155,991 | 5/1979 | Schopflin et al. | 128/260 |

OTHER PUBLICATIONS

Am. J. Obstet. Gynecol., Jan. 1, 1978, Mishell et al., pp. 55–62.
Am. J. Obstet. Gynecol., May 1, 1970, Mishell et al., pp. 100–107.
Contraception, vol. 12, No. 3, 9–1975, pp. 261–278, Victor et al.
Acta Obstet. Gynecol. Scand. Supply 54, 4–1976, Weiner et al., pp. 35–43.
Contraception, vol. 16, No. 2, Aug. 1977, Victor et al., pp. 137–147.
Contraception, vol. 14, No. 2, Aug. 1976, Victor et al., pp. 215–226.
Am. J. Obstet. Gynecol., vol. 117, No. 1, Sep. 1973, Henzl et al., pp. 101–106.
Fertility and Sterility, vol. 28, No. 8, Aug. 1977, Kragt et al., pp. 856–862.
Jour. Pharm. Sci., vol. 63, No. 4, Apr. 1974, Flynn et al., pp. 479–510.

Primary Examiner—Robert W. Michell
Assistant Examiner—C. F. Rosenbaum
Attorney, Agent, or Firm—Brumbaugh, Graves, Donohue & Raymond

[57] ABSTRACT

This invention relates to an improved intravaginal ring for use as a contraceptive comprising an inert elastomer core, a medicated layer encircling the core and an outer inert elastomer layer and method of manufacturing the intravaginal ring.

13 Claims, 11 Drawing Figures

Diffusion of levonorgestrel in vitro from IVRs with an outer layer of 0.4 mm. The 0.1mm medicated layer contains 10% levonorgestrel and 5% estradiol as described in Examples 19 and 20.

INTRAVAGINAL RING

BACKGROUND OF THE INVENTION

This invention relates to an intravaginal ring herein sometimes referred to as an IVR containing contraceptive steroids, a method of manufacturing the intravaginal rings and a method of contraceptive treatment in mammals using this intravaginal ring.

A variety of chemical and mechanical methods for controlling fertility and for preventing pregnancy are known. Approaches such as sterilization, the use of condoms, IUDs, spermicidal creams and jellies, foam tablets, and oral pills are currently available as a prevention against pregnancy. These methods, though effective to a variable extent, also have limitations. Most of the devices require constant motivation on the part of the user and some approaches such as sterilization and IUDs require specialized medical attention. The oral pill is a popular method of contraception but the oral contraceptives have many undesirable side effects and require the daily ingestion of a tablet. The use of the IVR as a means of administering effective contraceptive steroids through a vaginal route was seen as a means of overcoming some of these drawbacks.

Intravaginal rings are annularly shaped articles which can be introduced into the vagina in a simple manner without medical assistance. The IVR fits between the rear wall of the vagina and the upper edge of the pubic bone. The IVR device is primarily useful for the inhibition of fertility, that is contraceptive purposes, but is also used to treat and medicate other conditions. IVRs are designed so that they can be retained in the vagina for a period up to about one year. In routine contraceptive use, the ring is inserted in the vagina for 3 weeks, removed for one week and reinserted on a schedule of three weeks in, one week out.

Depending on the anatomy of the patient, the IVR may vary in size, for example from 45 mm to 65 mm in outer diameter. IVRs contain medication, for example, effective contraceptive steroids which diffuse through the IVR and are absorbed by the surrounding body fluid through the vaginal mucosa. The IVR exerts its medicative effect as long as the IVR is retained within the body and the supply of the medication is sufficient.

The concept of using intravaginal rings as a means of administering effective contraceptive steroids by absorption through the vaginal mucosa for contraceptive purposes was tested by Mishell and associates in 1970, Mishell, D. R. Jr., et al. Am. J. Obstet. Gynecol. 107:100, 1970.

The results of these tests indicated that IVRs containing an effective amount of contraceptive steroids offer a reliable and acceptable method of contraception. During the years from 1970 to 1975 a series of clinical studies with a variety of steroids and IVR designs were undertaken to develop a practical IVR. As a result of that work, IVRs containing effective contraceptive steroids have now been developed with several different designs and made from a wide variety of materials. A variety of inert elastomers or combinations of elastomers are suitable for making IVRs; for example, organopolysiloxanes of the linear type converted to rubber by various catalysts such as stannous octoates, platinum salts and peroxides and/or by heat provide a compatible nontoxic matrix for IVRs. Useful materials for making IVRs include, for example, conventional silicone rubber, Silastic 382[1], polyurethane, latex rubber, polyamides, polyesters, polytetrafluoroethylene, polyethylene vinyl acetate and nylon.

[1]Silastic is a trademark of Dow Corning Corporation for a silicone polymer.

There are four basic IVR designs, denominated for this description as the homogeneous IVR, the Schering IVR, the Roseman IVR, and the shell IVR. For further details on IVR designs, see *New Delivery Systems for D-Norgestrel*, Weiner et al., Acta Obstet Gynecol. Scand, Suppl. 54, 1977 p. 35, U.S. Pat. No. 3,920,805 to Roseman and U.S. Pat. No. 4,012,496 to Schöpflen.

In the homogeneous IVR, the contraceptive steroid is dispersed throughout an inert elastomer matrix as described in U.S. Pat. No. 3,545,439 to Duncan or in Victor et al., Contraception 12:261, 1975; see FIG. 3.

The Schering IVR consists of an inert elastomer ring encircled by a second ring of inert elastomer impregnated with a contraceptive steroid. For a discussion of this type of IVR see U.S. Pat. No. 4,012,496 to Schoepflin et al.

In the Roseman IVR a thin layer of an inert elastomer containing a contraceptive steroid is molded onto a central inert core of elastomer; see FIG. 5.

In the shell IVR, of which the present invention is an improvement, a thin medicated layer of an inert elastomer containing a contraceptive steroid surrounds a central inert core of synthetic elastomer and the medicated layer is surrounded by an outer layer of inert elastomer of variable thickness. The thickness of the outer layer is varied to control the release rate of the steroid; see FIG. 4. Clinical research with the shell IVR has been described in Mishell D. R., Jr. et al. *Clinical Performance and Endocrine Profiles with Contraceptive Vaginal Rings Containing a Combination of Estradiol and d-Norgestrel*, Am. J. Obstet Gynecol, 130:55 (1978); see also Weiner supra. The clinical acceptance of the shell design IVR thus far has been favorable.

The release of the contraceptive steroids from any of the four IVR designs is governed by Fick's law. According to Fick's law, as applied to systems with suspended solutes, the mass (M) transferred across a boundary per unit time (t) will be a function of the concentration of the mass at saturation ($C_s$) and the diffusion ($D_s$) and an inverse function of the distance across the boundary (h).

$$(dM/dt) = (D_s C_s / h)$$

When a drug such as a contraceptive steroid is suspended in a stationary matrix as in the IVR, h is the distance from the surface of the matrix to the plane in the matrix where the drug is located. When diffusion of the drug from the matrix occurs, the drug supply nearest the surface of the matrix will diffuse first and the distance h will increase as diffusion of the drug continues. This increase in the distance h from the surface of the matrix to the plane where the drug is located increases the time required for the drug to reach the surface and thereby decreases the amount of drug being transferred to the surface of the matrix per unit time. Based on Fick's law, it can be demonstrated[2] that the amount of drug transferred to the surface of the matrix will be a linear function of the square root of time.

[2]Flynn, G. L., Yalkowsky, S. H. and Roseman, T. J.: Mass transport phenomenona and models: Theoretical concepts. J. Pharm. Chem. 63 479-510, 1974.

In applying Fick's law to the diffusion of contraceptive steroids from various IVR designs, several factors must be considered. If the reservoir of contraceptive steroids in an IVR is dispensed uniformly throughout the IVR as in the homogeneous IVR, it is evident that the distance the steroid must travel to reach the surface of the IVR will increase markedly before the steroid reservoir is exhausted. The rate of release of the contraceptive steroid from the homogeneous IVR will decrease with time as the distance h increases. Similar release rate patterns are observed with the Schering IVR which in principal is similar to the homogeneous IVR.

The Roseman ring presents an improvement in IVR design in that the layer containing the steroid has been confined to a layer at the surface of the ring. However, in spite of this modification the rate of release of the steroid continues to decrease over time. The change in the distance which the steroid must travel to reach the surface of the ring still progresses from zero to a finite value and thus the relative proportional change in the rate is large and the release rate is not constant. If, however, the layer containing the contraceptive steroid is placed beneath a rate controlling layer as in the shell IVR a much more constant rate of release over time is obtained. The small proportional change in the distance the steroid must travel to reach the surface of the IVR between the time the IVR is first inserted ($t=0$) and the time when the supply of the contraceptive steroid is exhausted ($t=x$) is reflected in the more constant rate of release. These differences are illustrated in FIGS. 3, 4 and 5.

FIG. 3 shows a cross section of a homogeneous IVR, FIG. 4 shows a cross section of a shell IVR and FIG. 5 illustrates a cross section of a Roseman IVR. It can be seen from these figures that the distance $h_t=x$ is much greater for homogeneous IVRs than for the Roseman IVR and the shell IVR. For this reason both the shell IVR and the Roseman IVR are considered to be more useful designs for controlling release rates of steroids than the homogeneous IVR. By comparing FIGS. 4 and 5 it can be seen that the relative changes in distance between $h_t=0$ and $h_t=x$ will be less for the shell design IVR than for the Roseman IVR since in the shell IVR $h_t=0$ has a finite value. The relative change from $h_t=0$ to $h_t=x$ and the corresponding change in the release of medication observed with the Roseman IVR interfers with attempts to supply constant daily doses of contraceptive steroids to the patient, which is an important consideration in administering these steroids.

An additional drawback of previously developed IVRs is that with the exception of Duncan's IVR disclosed in U.S. Pat. No. 3,545,439, IVRs usually do not contain estrogen and contain only a progestationally active steroid alone and not in combination with estrogen. The use of progestionally active steroids alone in IVRs not in combination with estrogen leads to undesirable irregular breakthrough bleeding or spotting. Breakthrough bleeding is bleeding which occurs during the 21 day period when the IVR is in place. In unmedicated women, the intervals of about three weeks between menstrual bleeding events is usually free from bleeding and such bleeding is undesirable. Spotting is distinguished from breakthrough bleeding only in that a lesser amount of blood is voided. When the amount of blood is great enough that the woman feels that she needs the protection of a sanitary pad or tampon, the occurence is designated as "bleeding". When the amount of blood is less than this, it is designated as "spotting".

Estrogens have been known to improve bleeding and spotting control when administered orally in combination with other steroids in the oral contraceptive pill; however, estrogens are also known to cause a variety of undesirable metabolic changes especially in the liver. These changes are believed to increase the incidence of thromboembolisms, strokes and cardiac infarctions and for this reason estrogens have not been extensively used in IVRs to control breakthrough bleeding.

An improved shell IVR has now been found. The improvement comprises in combination, an inert elastomer core, a medicated layer attached to and encircling the core and an outer inert elastomer layer. The outer inert elastomer layer has a thickness of about 0.1 to 0.6 mm and the medicated layer has a thickness of not more than twice the thickness of the outer layer and contains an inert elastomer and a combination of estradiol-17$\beta$ with a progestogen selected from the group consisting of levonorgestrel, d,1-norgestrel and norethindrone.

The IVR has an inert core with an overall diameter of from about 45 mm to 65 mm preferably from 48 mm to 60 mm. The cross sectional diameter of the inert core is from about 5 mm to 10 mm, preferably from 7–9 mm. The medicated layer may be from about 0.05 to 1 mm thick with the provision that it is not more than twice the thickness of the outer layer, preferably 0.1 to 0.2 mm. The outer layer may be from about 0.1 to 0.6 mm thick preferably 0.2 mm. The thickness of the outer layer affects the distance the steroid must travel to reach the subjects system and thereby is used to control the release rate of the steroid.

The inert elastomer core can be constructed from the following classes of elastomer;

1. Thermosetting organopolysiloxanes to be vulcanized with peroxide curing catalysts, e.g. benzoyl peroxide or di-p-chlorobenzoyl peroxide at temperatures of about 200° C. and requiring a heat aftertreatment, e.g. those described in U.S. Pat. No. 2,541,137; 2,723,966; 2,863,846; 2,890,188 and 3,022,951.

2. Hydroxyl-terminated organopolysiloxanes of the RTV (room temperature vulcanizing) type which harden to elastomers at room temperature after the addition of cross-linking agents in the presence of curing catalysts and under the atmospheric humidity. Typical curing catalysts are metallic salts of carboxylic acids, preferably tin salts, e.g. tin (II) octoate and tin (II)-2-ethylhexanoate.

3. Single-component silicone rubber compositions which are cured at room temperature under atmospheric humidity without any further additives. These single component compositions contain primarily organopolysiloxanes with two terminal-positioned hydrolyzable acyloxy groups, e.g. acetoxy; the acyloxy groups are hydrolyzed under atmospheric humidity to form trifunctional siloxane units which crosslink the polymer into a cured elastomer. Such organopolysiloxanes are described, e.g., in U.S. Pat. Nos. 2,927,907 and 3,035,016 and in British Pat. Nos. 798,669 and 804,199.

4. Two-component dimethylpolysiloxane compositions, platinum-catalyzed at room temperature or under slightly elevated temperature and capable of addition cross-linking. The medicated layer can be constructed from an elastomer selected from classes 2 and 3 above and the outer layer can be constructed from an elastomer selected from classes 1 to 4 above, provided the elastomers in class 1 are cured before coming in contact with the medicated layer. The preferred elastomers for use in the core, medicated layer and the outer layer are polydimethylsiloxanes.

It is recognized, of course that other elastomers may be used in preparing the core.

The medicated layer contains an inert elastomer and a combination of estradiol-17β with progestogen selected from the group consisting of levonorgestrel, d-1-norestrel and norethindrone, preferably levonorgestrel. The amount of steroid used in the medicated layer is adjusted according to the expected total time of use of the IVR. It is necessary to add sufficient amounts of the steroids to prevent pregnancy throughout the period of expected use. A 30%–50% excess over average requirements is also provided to allow for variations in the absorbtion rate in different patients.

The amount of contraceptive steroids which can be used in the medicated layer is limited by the cost of the steroids and the amount of steroid that can be included in the medicated layer without weakening the structure or exceeding the dimensions of the ring. An IVR designed for one month's use requires about 3 to 10 mg of estradiol and about 4–20 mg of levonorgestrel to release an amount of the steroid sufficient to prevent pregnancy. If d,1-norgestrel is used in the IVR about 8–40 mg would be required. An IVR designed for 6 month's use requires about 20–120 mg of levonorgestrel preferably about 70 mg and about 15–50 mg of estradiol preferably about 35 mg. If d,1-norgestrel is used about 40–240 mg would be required. If norethindrone is used in a six month IVR about 60–200 mg preferably 120 mg would be required. An IVR designed for one year's use would contain about 30–100 mg of estradiol and about 40–240 mg of levonorgestrel. If d,1-norgestrel is used in the IVR, about 80–480 mg are required for one year's use.

The shell IVR of the present invention has a uniform rate of release of the steroid to the subject's system. Unlike the homogeneous IVR or the Roseman IVR, the shell IVR of this invention has a relatively uniform release rate over a 3 month to one year period.

It has further been found that the IVR of this invention can be used in a method of contraceptive treatment in humans with a reduction in breakthrough bleeding and with minimal effects on liver metabolism.

Studies conducted by Mishell et al. Am. J. Obstet. Gynecol. 130, No. 1 Jan. 1, 1978 conclude that women using IVRs of this invention containing both estradiol and levonorgestrel have significantly better bleeding patterns than those using IVRs of the same design but containing levonorgestrel alone and that they produce a minimal effect on liver metabolism.

Many of the undesirable side effects associated with the oral administration of estrogen are thought to be associated with changes in women's metabolism. Such metabolic changes result in several measurable changes in the women's system. Among the changes thought to be important are increased circulating levels of triglycerides, and angiotensinogen, increased levels of clotting factors I, II, VII, IX, X and XIII and decreased levels of antithrombin III. Other changes that also occur but are not clearly implicated in serious health effects include increase in circulating corticosteroid binding globulin, sex hormone binding globulin, certain transaminases, and ceruloplasmin.

In contrast to the changes observed when estrogens are administered orally, there have not been significant increases in circulating triglycerides, corticosteroid binding globulin or angiotensinogen in women using IVRs containing combinations of levonorgestrel and estradiol.

It is believed that there are two possible reasons that the effect on liver metabolism observed with orally administered combinations of progestins and estrogens are not observed with the IVR of this invention. First, the natural steroid, estradiol is used in the shell IVR of this invention instead of the synthetic steroids ethinyl estradiol or mestranol that are used in oral contraceptives. A second reason for fewer metabolic affects when contraceptive steroids are administered vaginally instead of orally may be that with the vaginal route of administration the steroids are diluted by passage through a major portion of the circulation system before they reach the liver. When they are administered orally, portal circulation carries material absorbed through the intestinal wall directly to the liver.

It has further been found that the shell IVR of the present invention can be manufactured by several different methods. One method consists of:
(a) forming an annular core ring of suitable inert elastomer by injecting the unvulcanized elastomer into a mold and allowing it to cure;
(b) removing the ring and dipping it in an mixture of an inert volatile solvent containing a mixture of contraceptive steroid and an inert unvulcanized elastomer adhesive;
(c) removing the ring from the mixture and allowing the solvent to evaporate;
(d) repeating steps b and c until a medicated layer of the desired thickness is obtained;
(e) dipping the ring from step d into a mixture of an inert unvulcanized elastomer in an inert volatile solvent and allowing the solvent to evaporate to form an outer layer; and
(f) repeating step e until an outer layer of the desired thickness is obtained.

Suitable inert elastomers for use in this process are listed above. Suitable inert volatile solvents without limitation are toluene, hexane, benzene, xylene, and other organic solvents with low solubility for the steroids. The mold is preferably made of brass.

A medicated layer of from 0.05 mm to 1 mm can be used provided the medicated layer is not more than twice the thickness of the outer layer. Preferably the medicated layer is 0.1–0.2 mm thick.

The outer layer is of variable thickness from 0.1 mm to 0.6 mm, preferably 0.2 mm. The outer layer controls the release rate of the steroid from the IVR and can be varied accordingly.

An alternative method of making shell IVRs of this invention consists of:
(a) forming a core rod of suitable inert elastomer by injecting the unvulcanized elastomer into a mold, and allowing it to cure;
(b) removing the resulting core rod and cutting it into lengths about 15.5 cm;
(c) bringing the rod to a constant weight by either heating at about 110° C. or allowing the rod to stand at room temperature.
(d) pulling it through a coating solution containing a mixture of an elastomer and a mixture of estradiol and a progestogen;
(e) dipping the coated rod in a catalyst solution such as toluene or another solvent which will not substantially dissolve the steroid and allowing the coating to polymerize;

(f) swelling a piece of tubing in a volatile organic solvent, and sliding it over the coated rod from step e and allowing the solvent to evaporate;

(g) trimming the excess tubing from the ends of the rod and applying a medical grade adhesive to the ends of the rod and to the surface of the rod close to the end;

(h) placing a second piece of swollen tubing of about 4 cm in length over both ends of the rod to form a ring and holding the ends of the rod together for 24 hours until the adhesive has cured.

Another alternative and preferred method of manufacturing shell IVRs of this invention consists of:

(a) forming an annular core ring of suitable inert elastomer by injecting the unvulcanized elastomer into a mold and allowing it to cure, removing the circular ring from the mold and cutting it open;

(b) bringing the open ring to a constant weight by either heating at about 110° C. or allowing the rod to stand at room temperature and pulling it through a coating solution containing an unvulcanized elastomer and mixture of estradiol and a progestogen;

(c) dipping the coated open ring in a catalyst solution in a solvent such as toluene which will not substantially dissolve the steriod and allowing the coating to polymerize;

(d) swelling a piece of tubing in a volatile organic solvent, fitting it over the open ring from step c and allowing the solvent to evaporate;

(e) trimming the excess tubing from the ends of the open ring and applying a medical grade adhesive to the ends of the open ring and to about 1 cm of the surface of the open ring close to the end;

(f) placing a second piece of swollen tubing of about 4 cm in length over both ends of the open ring to reform the ring, and (g) holding the ends of the open ring together for 1–2 minutes and allowing the adhesive to cure for about 24 hours.

Suitable solvents for use in swelling the tubing are heptane, hexane, or other non polar solvents in which the steroid is only slightly soluble.

DETAILED DESCRIPTION OF THE INVENTION

Figure 1:
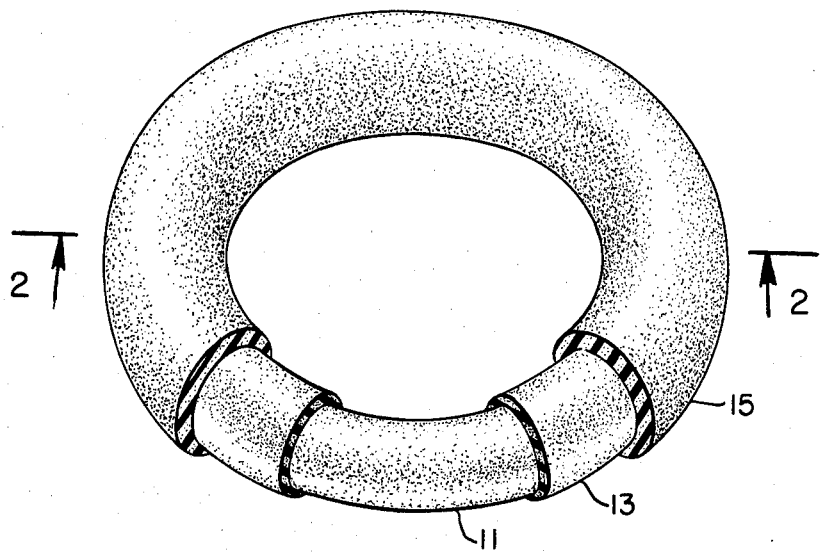
FIG. 1 is a perspective view partially cut away of the intravaginal ring of the present invention.
Figure 2:
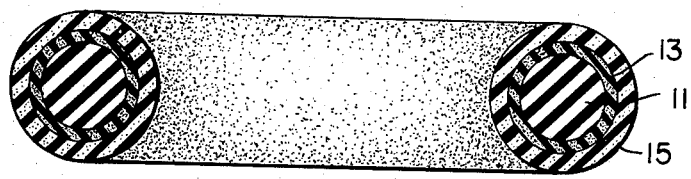
FIG. 2 is a sectional view through line 2,2 looking in the direction of the arrows of an intravaginal ring of the present invention.
Figure 3:
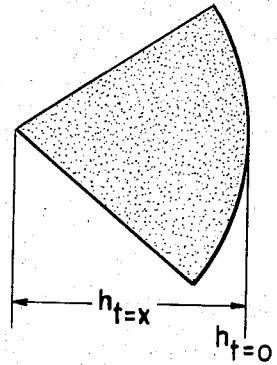
FIG. 3 is a sectional view of a quarter of a homogeneous intravaginal ring.
Figure 4:
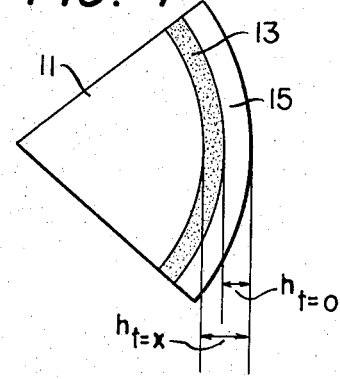
FIG. 4 is a sectional view of a quarter of an intravaginal ring of the present invention.
Figure 5:
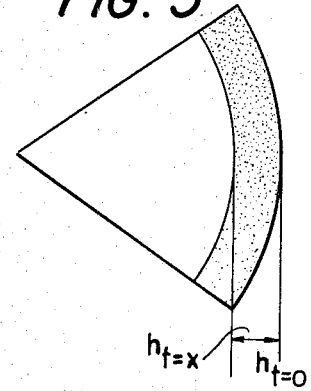
FIG. 5 is a sectional view of a quarter of a Roseman intravaginal ring.

With reference to FIGS. 1 and 2 the shell design IVR consists of a polysiloxane core 11, a medicated polysiloxane layer 13 encircling the core 11 and an outer layer 15 of polysiloxane tubing. The medicated layer 13 contains an inert elastomer and a combination of estradiol with a progestogen selected from the group consisting of levonorgestrel, d,1-norgestrel and norethindrone and the medicated layer 13 has a thickness of not more than twice the thickness of the outer layer.

The following examples illustrate the manner and process of making and using the shell IVR of this invention but are not to be construed as limiting.

EXAMPLE 1

A mixture of 9.7587 grams Silastic 382, 1.1650 grams of micronized levonorgestrel and 0.5755 grams of micronized estradiol were mixed in a Teflon bowl. The mixture was transferred to a Lucite coating cup with a bottom opening of 8.7 mm. A Dow Silastic rod 15.5 cm in length, prepared according to Example 3 below, was heated at 110° C. for 30 minutes, cooled and weighed. The cooled rod weighed 9.4090 grams. The rod was then pulled through the coating cup to provide a coating of the mixture thereon and then dipped in a solution of 0.67% stannous octoate in toluene (w/v). The coated rod was again heated at 110° C. for 30 minutes and reweighed. The weight of the coated rod was 9.6909 and the weight of the coating on the rod was therefore 0.2819 grams. The coating contained 28.6 mg levonorgestrel and 14.1 mg estradiol.

In order to apply the outer layer a 16.5 cm long piece of silicone rubber tubing having 6.3 mm diameter and 0.3 mm wall thickness was swollen in hexane and the rod coated with the medicated layer was placed inside the silicone rubber tubing. The hexane was evaporated at room temperature, leaving an outer wall of 0.2 mm. The tubing was trimmed flush with the ends of the rod and Dow Corning Medical Adhesive A was applied at both ends of the rod and to 1 cm of the outer layer at both ends of the rod. A 4 cm piece of silicone tubing 6.3 mm inner diameter and 0.3 mm wall thickness was swollen with hexane and placed over the two ends of the rod to form a ring. The ends of the rod were pressed together inside the tubing and the resulting ring was held in a clamp for 24 hours until the adhesive was cured.

EXAMPLE 2

A Dow Silastic 382 annular core 8.5 mm in cross section diameter and 57.5 mm overall diameter was prepared according to Example 4 below except the ring was not cut open. The resulting core ring weighted 9.7227 g. A mixture of 437 mg of levonorgestrel, 225 mg of estradiol-17$\beta$ and 1.985 of Dow Corning Medical Adhesive A in 8 ml of toluene was prepared. The Silastic core was mounted on an axle so that it could be diped and rotated through the mixture of steroids in the adhesive and toluene. After one complete rotation, the ring was removed form the bath to allow the toluene to evaporate. The ring was dipped and rotated through the bath three additional times and was then allowed to stand in the atmosphere and dry to a constant weight. The weight of the IVR was 10.1357 g. The medicated layer was 100 microns thick and the weight of the medicated layer was 413 mg. The coating contained 67 mg of levonorgestrel and 35 mg of estradiol.

A mixture of 2.99 g of Dow Medical Adhesive A in 10 ml toluene was prepared. The ring with the medicated layer was dipped into the mixture and rotated and removed. The toluene was allowed to evaporate. The ring was dipped and rotated through the mixture an additional two times and dried to a constant weight of 11.0607 g. The outer resin layer weighed 925 mg and was 0.1–0.2 mm thick.

EXAMPLE 3

Two silicone rubber rods, 20 cm long and 8.5 cm diameter were formed by injecting a mixture of 35 g of Dow Silastic 382 and 0.2 g stannous octoate into a brass mold. The mixture was allowed to stand in the mold for 45 minutes. The mold was opened and the rods were removed and cut into 15.5 cm lengths.

EXAMPLE 4

Four 58 mm core rings were usually prepared at a time. Fifty grams of Silastic 382 were mixed with 0.3 g of stannous octoate, transferred to a 50 cc plastic syringe and injected into four individual brass ring molds. After 45 minutes, the molds were opened, the rings removed, the flash was trimmed and the rings were cut open at a 45° angle. A mixture of 84.4 g Silastic 382, 12.2 g of micronized estrodiol and 24.4 g micronized levonorgestrel were mixed in a Teflon bowl. The mixture was transferred to a Lucite coating cup with a bottom opening of 8.7 mm. The open ring was heated at 110° C. for 30 minutes, cooled and weighed. The open ring weighed 9.8115 g. The open ring was pulled through the coating cup and dipped in a solution of 0.67% stannous octoate in toluene (w/v). The open ring was again heated at 110° C. for 30 minutes and reweighed. The weight of the coated open ring was 10.3564 g and the weight of the coating on the open ring was therefore 0.5449 g. The coating contained 112.0 mg levonorgestrel and 56.0 mg estradiol.

In order to apply the outer layer a 16.5 cm long piece of silicone rubber tubing having 6.3 mm diameter and 0.3 mm wall thickness was swollen in hexane and the open ring coated with the medicated layer was placed inside the silicone rubber tubing. The hexane was evaporated at room temperature and the tubing contracted to the size of the open ring forming an outer layer having a thickness of 0.2 mm.

The excess tubing was trimmed flush with the ends of the open ring and Dow Corning Medical Adhesive A was applied at both ends of the open ring and to 1 cm of the outer layer at both ends of the open ring. A 4 cm piece of silicone tubing 6.3 mm inner diameter and 0.3 mm wall thickness was swollen with hexane and placed over the two ends of the open ring to close the ring. The ring was held for about two minutes until the tubing shrank and fit snugly over the ring junction. The adhesive was allowed to cure for 24 hours, the rings were rinsed in alcohol and air dried.

Examples 5–25 below demonstrate the constant steroid release rate exhibited by the shell IVRs of the present invention as compared with the homogeneous IVR and the Roseman IVR, both of which exhibit high initial steroid levels which decline with time.

The weights of the rods coated and uncoated and the amounts of estradiol and levonorgestrel for the rings and rods used in the examples are presented in Tables 1 and 2.

EXAMPLE 5

Figure 6:
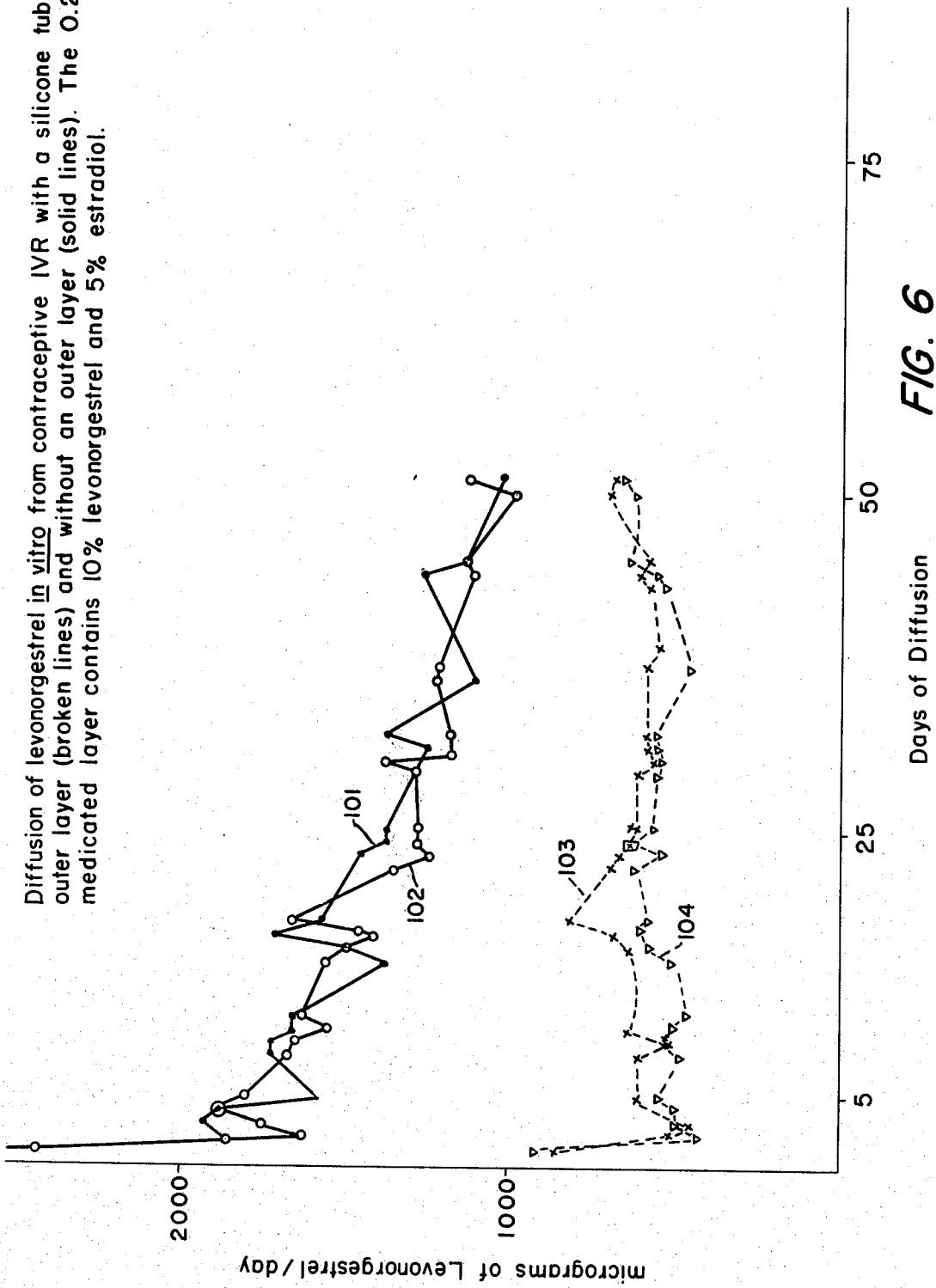
FIG. 6 is a graph showing diffusion of levonorgestrel in vitro from contraceptive IVRs with a silicone tubing outer layer (broken lines) and without an outer layer (solid lines). The 0.2 mm medicated layer contains 10% levonorgestrel and 5% estradiol as described in Examples 5, 6, 7 and 8.

An IVR 58 mm in overall diameter was prepared according to the procedure described in EX. 1.[2] The IVR was designated No. 103 and had a medicated layer 0.2 mm in thickness and an outer layer Of 0.2 mm. The IVR was suspended with plastic thread in a 600 ml tall form beaker and bathed in a 1:750 solution of benzalkonium chloride. The beaker containing the IVR was placed in a 37° C. shaking water bath. Each day the solution was changed and an aliquot analyzed for levonorgestrel by measuring the solution's absorbance at 240 namometers in a spectrophotometer and plotted against time. Estradiol was measured by the method of Mishell et al. *Serum Gonadotropins and Steroid Patters during a Normal Menstrual Cycle*, Am. J. Obstet, and Gynecol. Vol. 111, p. 60, 1971. The release rate of levonorgestrel is shown in FIG. 6 and the data are presented in Table 3. The data from the estradiol assays are presented in Table 4.

[2]The method of preparation described in Example 1 is used in the in vitro rate studies because the technique of coating a rod rather than an opened ring results in more uniform coatings and is thus preferable for the rate tests rather than the procedure described in Example 4 which is used for the in vivo tests.

EXAMPLE 6

The procedure described in Example 5 was repeated except the IVR was designated 104 and had a 0.2 mm medicated layer and an outer layer of 0.2 mm. The release rate of levonorgestrel is shown in FIG. 6 and the data are presented in Table 3. The data from the estradiol assays are presented in Table 4.

EXAMPLE 7

A 58 mm IVR was prepared according to the process described in Example 5 except that no outer layer was applied to the IVR. The IVR was designated 101 and had a 0.2 mm medicated layer and no outer layer. The release rate of levonorgestrel is shown in FIG. 6 and the data are presented in Table 5. The data from the estradiol assays are presented in Table 6.

EXAMPLE 8

A 58 mm IVR was prepared according to the process described in Example 5 except that no outer layer was applied to the IVR. The IVR was designated 102 and had a medicated layer 0.2 mm thick and no outer layer. The release rate of levonorgestrel is shown in FIG. 6 and the data are presented in Table 5. The estradiol data are presented in Table 6.

The results from Ex. 5-8 illustrated in FIG. 6 show that the IVRs of the invention, that is 104 and 103 contain about the same amount of steroid as those in 101 and 102 but IVRs 104 and 103 with the 0.2 mm outer layer give a lower initial steroid dose and release the levonorgestrel and estradiol at a more constant rate.

EXAMPLE 9

Figure 7:
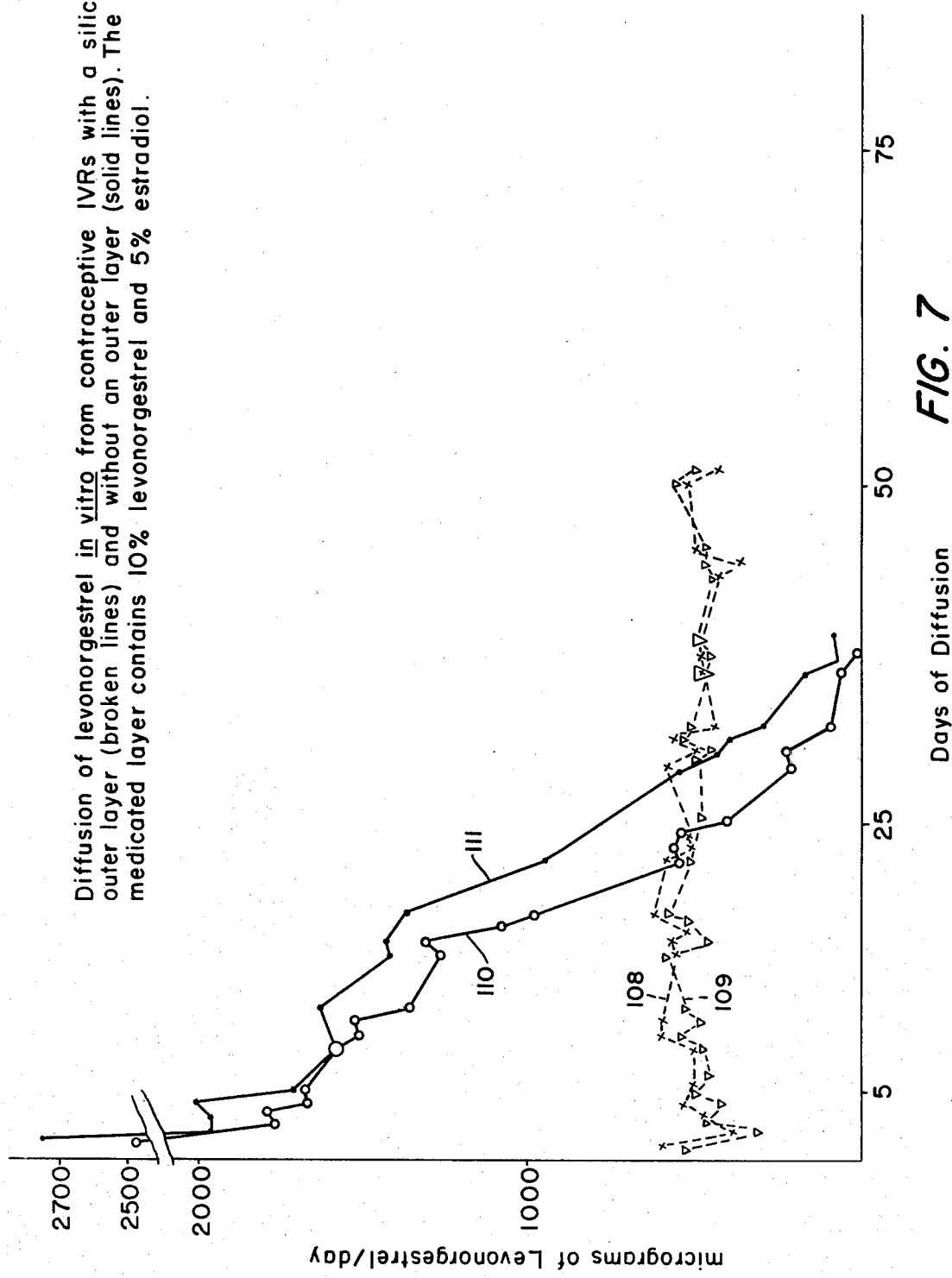
FIG. 7 is a graph showing diffussion of levonorgestrel in vitro from contraceptive IVRs with a silicone tubing outer layer (broken lines) and without an outer layer (solid lines). The 0.1 mm medicated layer contains 10% levonorgestrel and 5% estradiol as described in Examples 9, 10, 11 and 12.

The procedure described in Example 5 was repeated except the IVR was designated 108 and had a medicated layer 0.1 mm thick and had an outer layer 0.2 mm thick. The release rate of levonorgestrel is shown in FIG. 7 and the data are presented in Table 7. The estradiol data are presented in Table 8.

EXAMPLE 10

The procedure described in Example 5 was repeated except the IVR was designated 109 and had a medicated layer 0.1 mm thick and had an outer layer 0.2 mm thick. The release rate of levonorgestrel is shown in FIG. 7 and the data presented in Table 7. The estradiol data are presented in Table 8.

EXAMPLE 11

The procedure described in Example 5 was repeated except no outer layer was applied and the IVR was designated 110 and had a medicated layer 0.1 mm thick and no outer layer. The release rate of levonorgestrel is shown in FIG. 7 and the data are presented in Table 9. The estradiol data are presented in Table 10.

EXAMPLE 12

The procedure described in Example 5 was repeated except no outer layer was applied and the IVR was designated 111 and had a medicated layer 0.1 mm thick and no outer layer. The release rate of levonorgestrel is shown in FIG. 7 and the data are presented in Table 9. The estradiol data are presented in Table 10.

The results from Ex. 9-12 illustrated in FIG. 7 show that the IVRs of this invention (109, 108) contain about the same amounts of steroid as those outside the invention (110, 111) but IVRs 109 and 108 with the 0.2 mm outer layer give a lower initial dose and retain an effective level longer and releases the levonorgestrel and estradiol at a more constant rate. In fact, after 37½ days the levonorgestrel was depleted from IVRs 110 and 111.

EXAMPLE 13

Figure 8:
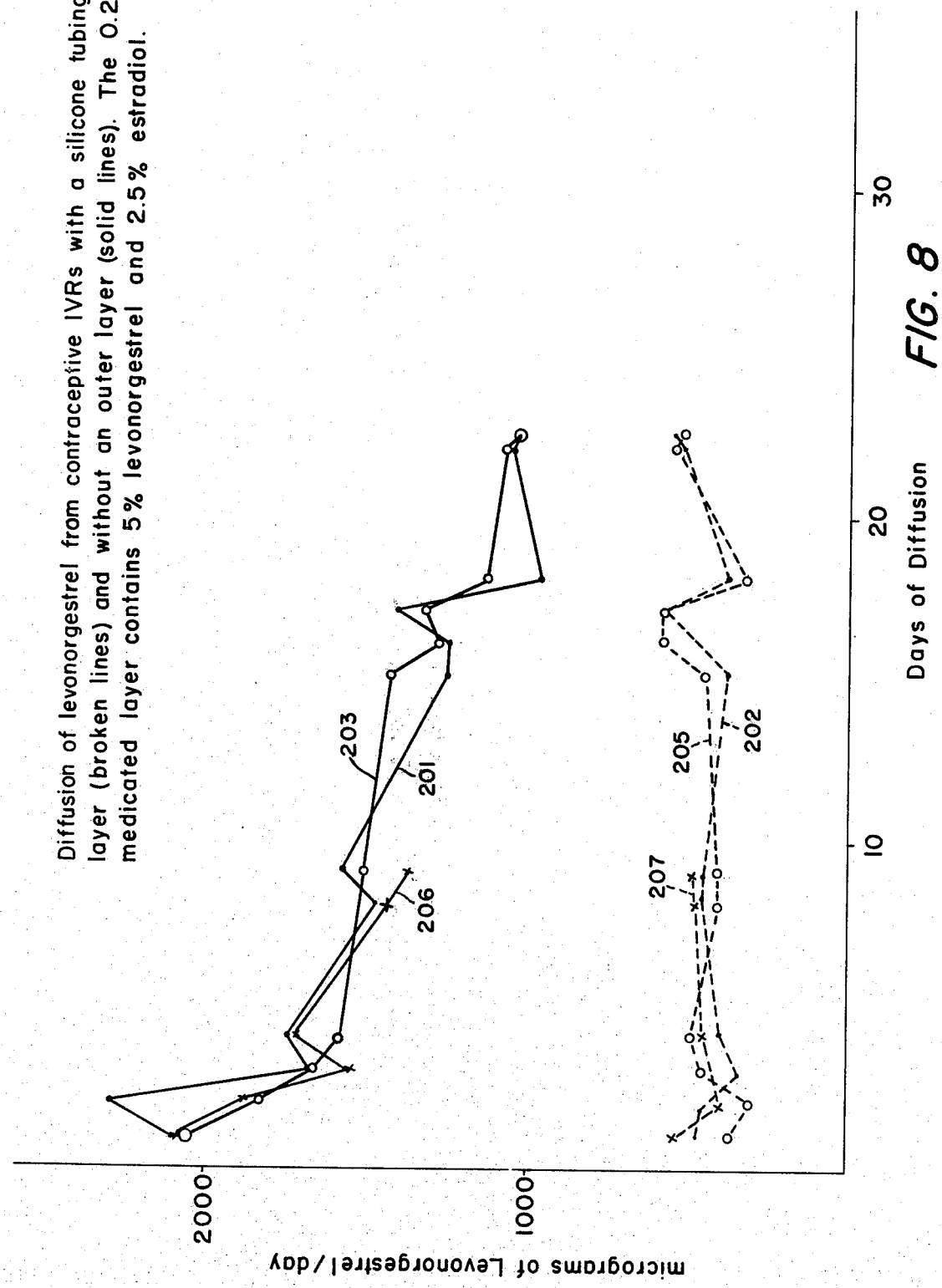
FIG. 8 is a graph showing diffusion of levonorgestrel from contraceptive IVRs with a silicone tubing outer layer (broken lines) and without an outer layer (solid lines). The 0.2 mm medicated layer contains 5% levonorgestrel and 2.5% estradiol as described in Examples 13, 14, 15, 16, 17 and 18.

A 58 mm IVR was prepared according to the process described in Ex. 5 except that no outer layer was applied to the IVR. The IVR was designated 201 and had a medicated layer 0.2 mm thick and with no outer layer. The release rate of levonorgestrel is shown in FIG. 8 and the data are presented in Table 11. The estradiol data are presented in Table 12.

EXAMPLE 14

The procedure as described in Example 5 was repeated. The IVR was designated 203 and had an 0.2 mm medicated layer and no outer layer. The release rate of levonorgestrel is shown in FIG. 8 and the data are presented in Table 11. The estradiol data are presented in Table 12.

Example 15

The procedure as described in Example 5 was repeated except the IVR was designated 206 and had a 0.2 mm medicated layer and no outer layer. Partial results of the levonorgestrel and the estradiol assays are shown in FIG. 8. Since Examples 13, 14 and 15 were triplicate samples after 9 days sample 206 was not analyzed.

EXAMPLE 16

The procedure described in Example 5 was repeated except that the IVR was designated 202, had an 0.2 mm medicated layer and an 0.2 mm outer layer. The release rate for levonorgestrel is shown in FIG. 8 and the data is presented in Table 11. The estradiol data are presented in Table 12.

EXAMPLE 17

The procedure described in Example 5 was repeated except the IVR was designated 205 and had a medicated layer, 0.2 mm thick and an outer layer 0.2 mm thick. The release rate of levonorgestrel is shown in FIG. 8 and the data are presented in Table 11. The estradiol data are presented in Table 12.

EXAMPLE 18

The procedure described in Example 5 was repeated except that the IVR was designated 207 and had a medicated layer, 0.2 mm thick and 0.2 mm outer layer. The partial results of the levonorgestrel are shown in FIG. 8. As in Example 15 this sample was not analyzed after 9 days.

The results from Examples 13-18 illustrated in FIG. 8 show that the IVRs of this invention (202, 205) contain about the same amount of steroid as those outside the invention (201, 203) but IVRs 202 and 205 with the 0.2 mm outer layer gave a lower initial dose and released levonorgestrel and estradiol at a more constant rate.

EXAMPLE 19

Figure 9:
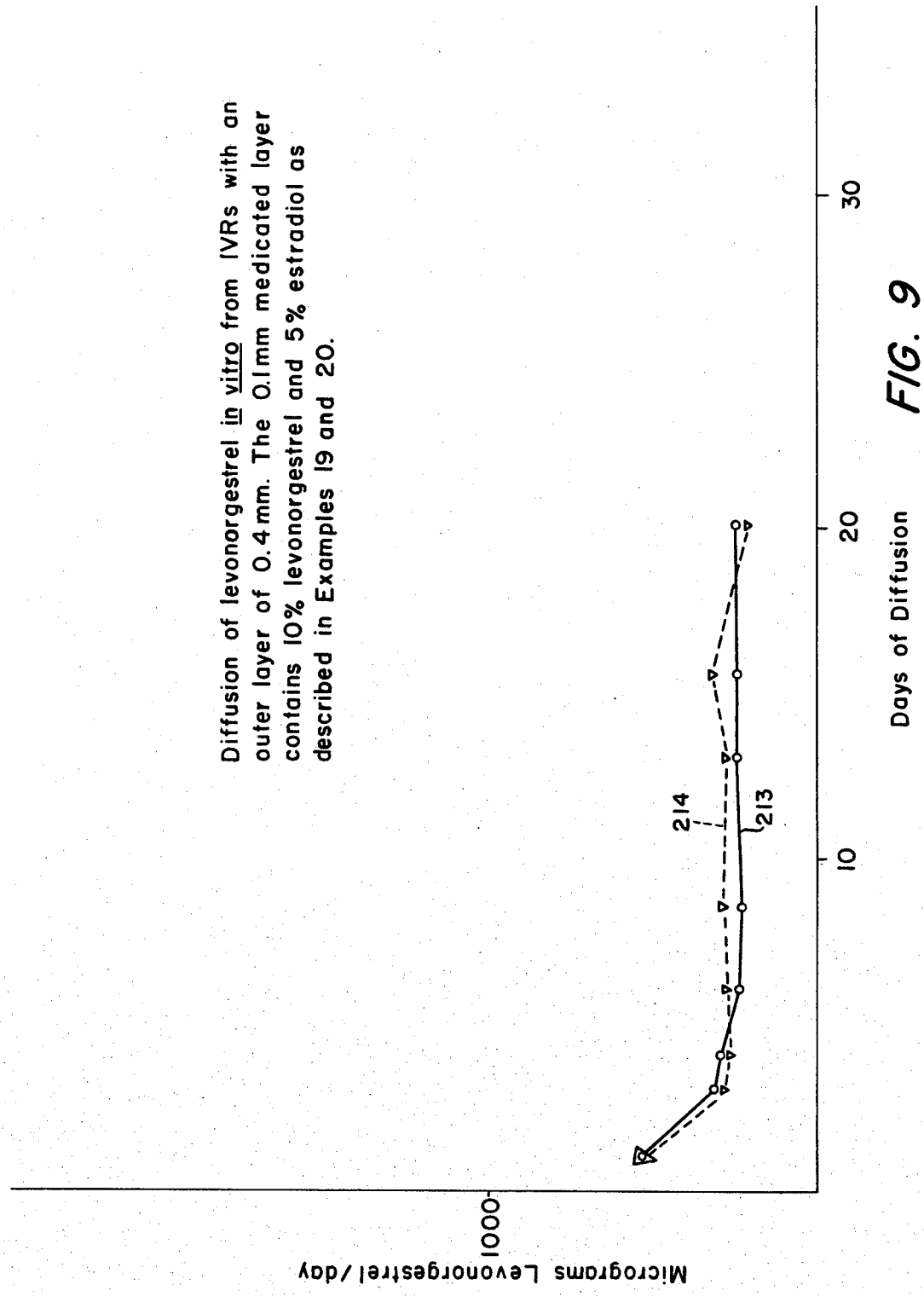
FIG. 9 is a graph showing diffusion of levonorgestrel in vitro from IVRs with an outer layer of 0.4 mm. The 0.1 mm medicated layer contains 10% levonorgestrel and 5% estradiol as described in Examples 19 and 20.

The procedure described in Example 5 was repeated except the IVR was designated 213 and had a 0.1 mm medicated layer and an outer layer 0.4 mm thickness. The release rate of levonorgestrel is shown in FIG. 9 and the data are presented in Table 13.

EXAMPLE 20

The procedure described in Example 5 was repeated except the IVR was designated 214 and had an 0.1 mm medicated layer and an outer layer 0.4 mm thickness. The release rate of levonorgestrel is shown in FIG. 9 and the data are presented in Table 13.

The lower rates of release observed with IVRs Nos. 213 and 214, as compared with Nos. 107 and 108, which are similar except for the thickness of the outer layer illustrate the role of the outer layer in controlling release rates. Examples 21-24 below illustrate the release rates obtained from prior art homogeneous IVRs.

EXAMPLE 21

A homogeneous contraceptive IVR containing 70 mg levonorgestrel and 35 mg estradiol and designated H-70-1 was suspended with plastic thread in a 600 ml tall form beaker and bathed in a 1:750 solution of benzalkonium chloride. The beaker containing the IVR was placed in a 37° shaking water bath. Each day the solution was changed and an aliquot analyzed for levonorgestrel by measuring the solution's absorbance at 240 nanometers in a spectrophotometer. Estradiol was measured by standard radioimmunoassay techniques. The release rate of levonorgestrel is shown in FIG. 10 and the data presented in Table 14.

EXAMPLE 22

Figure 10:
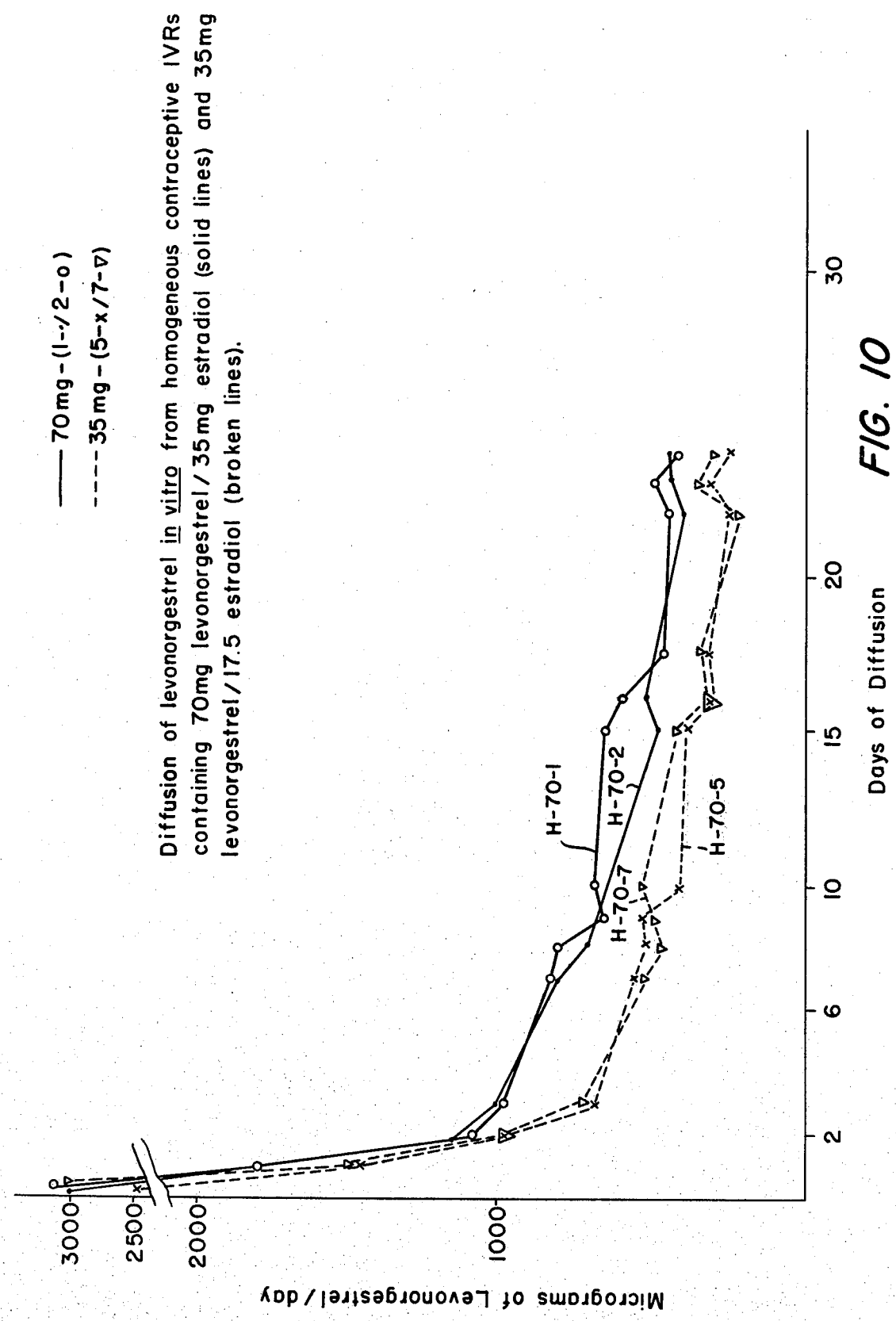
FIG. 10 is a graph showing diffusion of levonorgestrel in vitro from homogeneous contraceptive IVRs containing 70 mg levonorgestrel/35 mg estradiol (solid lines) and 35 mg levonorgestrel/17.5 mg estradiol (broken lines) as described in Examples 21, 22, 23 and 24.

The procedure of Example 21 was repeated except the homogeneous IVR was designated H-70-2 and the release rate of of levonorgestrel is shown in FIG. 10 and the data are presented in Table 14.

EXAMPLE 23

The procedure of Example 21 was repeated except the homogeneous IVR was designated H-70-5 and contained 35 mg levonorgestrel and 17.5 mg estradiol. The release rate of levonorgestrel is shown in FIG. 10 and the data are presented in Table 14.

EXAMPLE 24

The procedure of Example 23 was repeated except that the IVR was designated H-70-7. The release rate of levonorgestrel is shown in FIG. 10 and the data are presented in Table 14.

The results shown in FIG. 10 illustrate that homogeneous IVRs give high initial doses of levonorgestrel and the daily release rate decreases with time.

EXAMPLE 25

Figure 11:
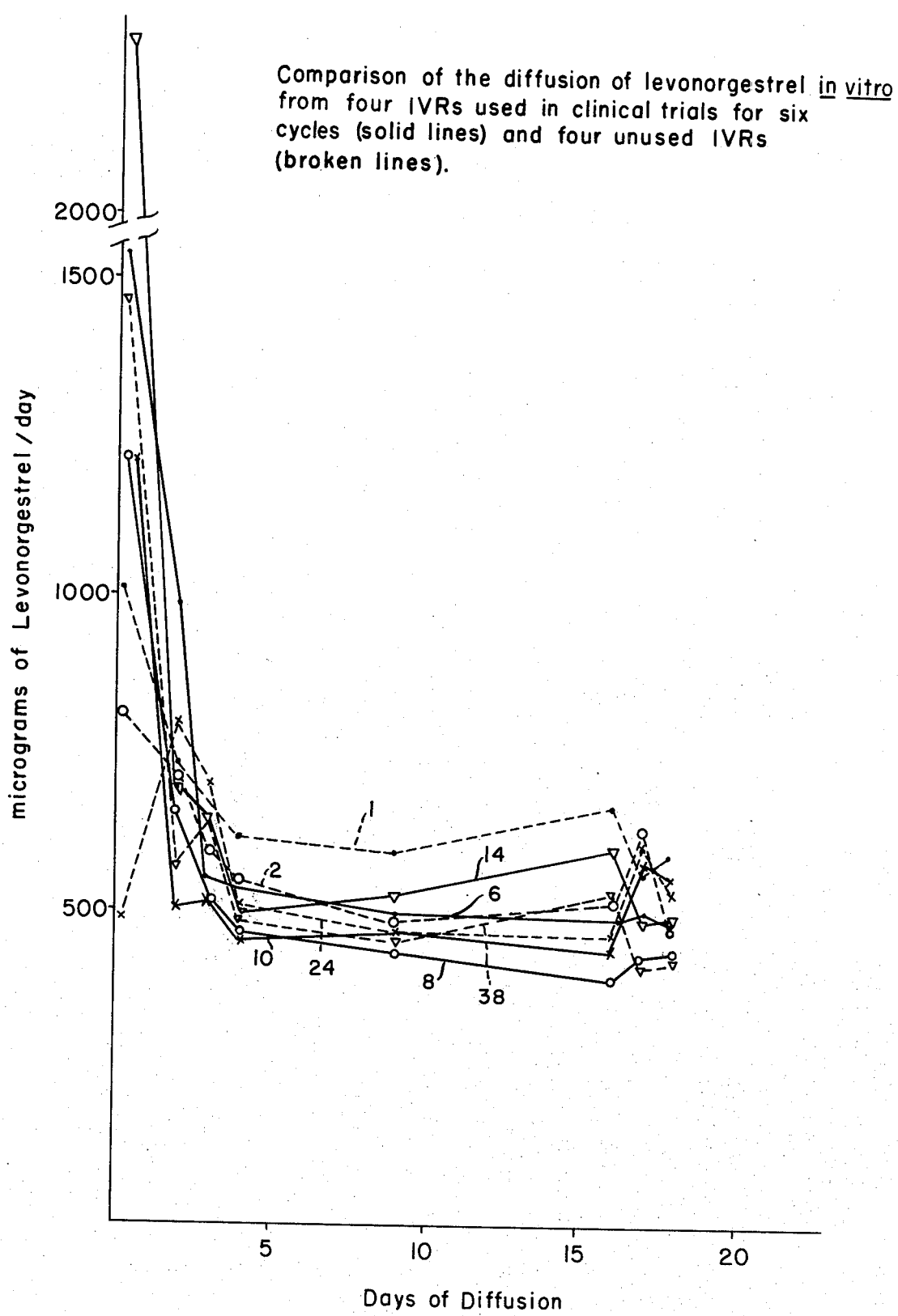
FIG. 11 is a graph showing a comparison of the diffusion of levonorgestrel in vitro from four IVRs used in clinical trials for six cycles (solid lines) and four unused IVRs (broken lines) as described in Example 25.

Eight IVRs were prepared according to the procedure of Example 4 having a medicated layer of about 0.15 mm and an outer layer of about 0.2 mm and designated 6, 8, 10, 14, 1, 2, 24 and 38. IVRs 6, 8, 10 and 14 were used by female subjects in clinical trials during six menstrual cycles. At the end of the six cycles the IVRs were tested as described in Example 5. The release rate of levonorgestrel for the four used IVRs 6, 8, 10 and 14 is shown in FIG. 11 in graphs with the solid lines. The data are presented in Table 15.

The four IVRs 1, 2, 24 and 38 which were not used in clinical trials were subjected to the same rate measuring test described in Example 5 and the release rate of levonorgestrel is shown in FIG. 11 by the broken line graphs and the data are presented in Table 15. It can be seen from these results there is no significant difference in the release rate of levonorgestrel between the used and unused IVRs. It is significant that after a six month period of use in human patients no significant decrease in the drug release or rate of release was observed.

Studies have been conducted in which bleeding patterns, triglyceride levels, angiotensinogen levels and corticosteroid binding globulin levels have been compared in patient groups using four different oral contraceptives Ovcon[4] 50, Ortho-Novum[5], Lo/Ovral[6], and Neocon and the IVRs of this invention. The results of these tests are summarized in Tables 16-20 discussed in detail below. The results show that IVRs of this invention containing estradiol and levonorgestrel produce fewer changes in the measured indicators of liver metabolism than oral contraceptives containing estrogen and results in better control of breakthrough bleeding and spotting.

[4] Ovcon is the registered trademark of Mead Johnson [5] Ortho-Novum and Neocon are the registered trademarks of Ortho Pharmaceutical, Inc. [6] Lo/Ovral is the registered trademark of Wyeth Laboratories

EXAMPLE 26

In order to compare shell IVRs containing levonorgestrel alone with those containing a mixture of levonorgestrel and estradiol and the effect of the addition of estradiol on breakthrough bleeding, 20 shell IVRs (58 mm) were prepared according to Example 4 having a medicated layer of about 0.15 mm and having an outer layer of about 0.2 mm. The IVRs were designated DE2-13, DE2-14, DE2-15, DE2-17, DE2-18, DE3-1, DE3-2, DE3-3, DE3-s4, DE3-5, DE3-6, DE3-8, DE3-9, DE3-10, DE3-13, DE4-1, DE4-2, DE4-3, DE4-4, DE4-5. Ten additional shell IVRs were prepared according to Example 4 having a medicated layer about 0.15 mm thick but containing only levonorgestrel and having an outer layer about 0.2 mm thick. The IVRs were designated D11-1, D11-2, D11-3, D12-9, D12-12, D12-13, D12-18, D12-19, D12-20, D12-27.

The IVRs were properly placed in the subjects. The ring fit securely and comfortably between the rear wall of the vagina and the upper edge of the pubic bone. The ring was removed for one week by the subjects to allow withdrawal bleeding and subsequently reinserted by the subjects and removed on a schedule of 3 weeks in and one week out for six months. Blood serum samples were taken from each subject at frequent intervals in the first 48 hours following each insertion of the IVR and three times per week thereafter. The women reported all occasions of breakthrough bleeding. The results of the study are listed in Table 16.

Table 16 below shows that the IVRs containing a combination of levonorgestrel and estradiol produce fewer instances of breakthrough bleeding and spotting than IVRs containing levonorgestrel alone.

EXAMPLE 27

Ten IVRs (50 mm) were prepared according to the description in Example 4 having a medicated layer of about 0.15 mm and an outer layer of about 0.2 mm. The IVRs were designated DE9-1, DE9-2, DE9-3, DE9-4, DE9-5, DE9-7, , DE9-8, DE9-9, DE9-10, DE9-11 and details regarding this preparation are found in Table 2. One was placed in the vagina of each of 10 women subjects on the fifth day of their menstrual cycle and left in place for 6 months. The IVR was properly placed when the ring fit securely and comfortably between the rear wall of the vagina and the upper edge of the pubic bone. The IVR was removed for one week by the subjects to allow withdrawal bleeding and subsequently reinserted by the subjects and removed on a schedule of 3 weeks in and one week out for six months. Blood serum samples were taken from each subject at frequent intervals in the first 48 hours following each insertion of the IVR and three times per week thereafter. The women reported all occasions of breakthrough bleeding.

The blood serum samples were tested for triglycerides, and corticosteroid-binding globulin and angiotensinogen levels. The triglyceride levels were measured according to standard published procedures. The corticosteroid-binding globulin level was measured by the method recently described by Moore et al., *An In Vivo System in Human for Quantitation of Estroginecity. I. Physiologic Changes in Serum Corticosteroid-Binding Capacity Levels*, Am. J. Obstet Gynecol, Feb. 15, 1978, Vol. 130, P. 475. The angiotensinogen levels were measured by a method described in Helmer and Judson Circulation 27:1050, 1963 and Haber et al. J. Chem. Endocrinol. Metab 29:1349.

The women reported all occasions of breakthrough bleeding.

The results of this experiment are summarized in Tables 17–20 infra. Table 17 shows the patient distribution during the 12 month test period.

EXAMPLE 28

Sixteen (16) women were given Ovcon 50 brand oral contraceptives daily according to the manufacturer's published directions. Blood samples were taken from the subjects according to the schedule of Example 27. The blood serum samples were tested for triglyceride, and corticosteroid-binding globulin and angiotensinogen levels as in Example 27. The women also reported all occasions of breakthrough bleeding.

The results of this experiment are summarized in Tables 18–20 supra. As can be seen from the tables not all subjects were able to continue through the entire experiment therefore the number of subjects in all Examples varied as indicated in Table 17.

EXAMPLE 29

Twelve (12) women were given Ortho Novum brand oral contraceptives daily according to the manufacturer's published directions. Blood samples were taken from the subjects according to the schedule of Example 27. The blood serum samples were tested for triglyceride, and corticosteroid-binding globulin and angiotensinogen levels as in Example 27. The women also reported all occassions of breakthrough bleeding. The results of this experiment are summarized in Tables 18–20 supra.

EXAMPLE 30

Seventeen (17) women were given Lo/Ovral brand oral contraceptives daily according to the manufacturer's published directions. Blood samples were taken from the subjects according to the schedule of Example 27. The blood serum samples were tested for triglyceride, and corticosteroid-binding globulin and angiotensinogen levels as in Example 27. The women also reported all occasions of breakthrough bleeding. The results of this experiment are summarized in Tables 18–20 supra.

EXAMPLE 31

Twelve (12) women were given Neocon brand oral contraceptives daily according to the manufacturer's published directions. Blood samples were taken from the subjects according to the schedule of Example 27. The blood serum samples were tested for triglyceride and corticosteroid-binding globulin and angiotensinogen levels as in Example 27. The women also reported all occasions of breakthrough bleeding. The results of this experiment are summarized in Tables 18–20 supra.

The results from Examples 26–31 show that less breakthrough bleeding and spotting and fewer metabolic changes are observed in patients using shell IVRs containing levonorgestrel and estradiol than in patients taking oral contraceptives.

TABLE 1

| Example No. | IVR No. | Silastic 382 | Levonorgestrel | Estradiol |
|---|---|---|---|---|
| 5 | 103 | 9.7587 | 1.1650 | 0.5755 |
| 6 | 104 | 9.7587 | 1.1650 | 0.5755 |
| 7 | 101 | 9.7587 | 1.1650 | 0.5755 |
| 8 | 102 | 9.7587 | 1.1650 | 0.5755 |
| 9 | 108 | 9.7587 | 1.1650 | 0.5755 |
| 10 | 109 | 9.7587 | 1.1650 | 0.5755 |
| 11 | 110 | 9.7587 | 1.1650 | 0.5755 |
| 12 | 111 | 9.7587 | 1.1650 | 0.5755 |
| 13 | 201 | 9.2585 | 0.4905 | 0.2538 |
| 14 | 203 | 9.2585 | 0.4905 | 0.2538 |
| 15 | 206 | 9.2585 | 0.4905 | 0.2538 |
| 16 | 202 | 9.2585 | 0.4905 | 0.2538 |
| 17 | 205 | 9.2585 | 0.4905 | 0.2538 |
| 18 | 207 | 9.2585 | 0.4905 | 0.2538 |
| 19 | 213 | 15.2869 | 1.8216 | 0.9001 |
| 20 | 214 | 15.2869 | 1.8216 | 0.9001 |
| 25 | 6 | 63.2235 | 18.0722 | 9.7556 |
|  | 8 | 63.2235 | 18.0722 | 9.7556 |
|  | 10 | 63.2235 | 18.0722 | 9.7556 |
|  | 14 | 63.2235 | 18.0722 | 9.7556 |
|  | 1 | 63.2235 | 18.0722 | 9.7556 |
|  | 2 | 63.2235 | 18.0722 | 9.7556 |
|  | 24 | 63.2235 | 18.0722 | 9.7556 |
|  | 38 | 63.2235 | 18.0722 | 9.7556 |
| 26 | DE2-13, DE2-14, DE2-15, DE2-17, DE2-18 | 7.0310 | 2.0360 | 1.0232 |
|  | DE3-1, DE3-2, DE3-3, DE3-4, DE3-5, DE3-6, DE3-8, DE3-9, DE3-10, DE3-13 | 7.0775 | 2.0185 | 1.0071 |
|  | DE4-1, DE4-2, DE4-3, DE4-4, DE4-5 | 14.0280 | 4.0171 | 2.0111 |
|  | D11-1, D11-2, D11-3 | 3.0279 | 1.0118 | — |
|  | D12-9 | 6.2689 | 1.5333 | — |
|  | D12-12, D12-13, D12-18 | 6.4994 | 1.2358 | — |
|  | D12-19, D12-20, D12-27 | 6.4621 | 1.4607 | — |
| 27 | DE9-1, DE9-2, DE9-3, DE9-4, DE9-5, DE9-7, DE9-8, DE9-9, DE9-10, DE9-11 | 14.1554 | 4.3525 | 2.0526 |

TABLE 2
Composition of IVRs used in Examples

| Ex. No. | IVR No. | uncoated wt. of rod or ring(grams) | coated wt. of rod or ring(grams) | wt. gain (grams) | mg levonorgestrel/IVR | mg Estradiol/IVR | thickness(mm) medicated layer | thickness(mm) outer layer |
|---|---|---|---|---|---|---|---|---|
| 5 | 103 | 9.7531 | 10.4153 | 0.6620 | 67 | 33 | 0.2 | 0.2 |
| 6 | 104 | 9.2877 | 10.0350 | 0.7473 | 76 | 37 | 0.2 | 0.2 |
| 7 | 101 | 9.7585 | 10.4692 | 0.7107 | 72 | 36 | 0.2 | none |
| 8 | 102 | 9.7425 | 10.3658 | 0.6233 | 63 | 31 | 0.2 | none |
| 9 | 108 | 9.4090 | 9.6909 | 0.2819 | 29 | 14 | 0.1 | 0.2 |
| 10 | 109 | 9.7892 | 10.1075 | 0.3183 | 32 | 16 | 0.1 | 0.2 |
| 11 | 110 | 9.7590 | 10.0935 | 0.3345 | 34 | 17 | 0.1 | none |
| 12 | 111 | 9.7886 | 10.0416 | 0.2530 | 26 | 13 | 0.1 | none |
| 13 | 201 | 9.4431 | 10.1794 | 0.7363 | 36 | 19 | 0.2 | none |
| 14 | 203 | 9.6276 | 10.3554 | 0.7278 | 36 | 18 | 0.2 | none |
| 15 | 206 | 9.7732 | 10.4836 | 0.7104 | 35 | 18 | 0.2 | none |
| 16 | 202 | 9.7900 | 10.5615 | 0.7715 | 38 | 20 | 0.2 | 0.2 |
| 17 | 205 | 9.5820 | 10.3016 | 0.7196 | 35 | 18 | 0.2 | 0.2 |
| 18 | 207 | 9.4835 | 10.1277 | 0.6442 | 32 | 16 | 0.2 | 0.2 |
| 19 | 213 | 9.7276 | 10.0916 | 0.3640 | 37 | 18 | 0.1 | 0.4 |
| 20 | 214 | 9.6705 | 10.0307 | 0.3602 | 36 | 18 | 0.1 | 0.4 |
| 25 | 6 | 9.6536 | 10.3002 | 0.6466 | 134 | 66 | 0.1 | 0.2 |
|  | 8 | 9.5458 | 10.1752 | 0.6264 | 130 | 64 | 0.15 | 0.2 |
|  | 10 | 9.8422 | 10.3955 | 0.5533 | 115 | 57 | 0.15 | 0.2 |
|  | 14 | 9.6704 | 10.2740 | 0.6036 | 125 | 62 | 0.15 | 0.2 |
|  | 1 | 9.6830 | 10.2700 | 0.5870 | 122 | 60 | 0.15 | 0.2 |
|  | 2 | 9.7480 | 10.3362 | 0.5822 | 122 | 60 | 0.15 | 0.2 |
|  | 24 | 9.4231 | 10.0598 | 0.6367 | 132 | 65 | 0.15 | 0.2 |
|  | 38 | 9.7124 | 10.2600 | 0.5476 | 114 | 56 | 0.15 | 0.2 |
| 26 | DE2-13 | 10.6196 | 10.9005 | 0.2836 | 57 | 29 | 0.15 | 0.2 |
|  | DE2-14 | 10.6341 | 10.9660 | 0.3319 | 67 | 34 | 0.15 | 0.2 |
|  | DE2-15 | 10.6569 | 10.9792 | 0.3223 | 65 | 33 | 0.15 | 0.2 |
|  | DE2-17 | 10.5813 | 10.9367 | 0.3554 | 72 | 36 | 0.15 | 0.2 |
|  | DE2-18 | 10.7131 | 11.0945 | 0.3814 | 77 | 39 | 0.15 | 0.2 |
|  | DE3-1 | 9.3773 | 9.6752 | 0.2979 | 62 | 29 | 0.15 | 0.2 |
| 26 | DE3-2 | 9.6781 | 10.0385 | 0.3604 | 75 | 36 | 0.15 | 0.2 |
|  | DE3-3 | 9.7270 | 10.0550 | 0.3280 | 68 | 32 | 0.15 | 0.2 |
|  | DE3-4 | 9.8154 | 10.1558 | 0.3404 | 70 | 34 | 0.15 | 0.2 |
|  | DE3-5 | 9.7117 | 10.0128 | 0.3011 | 62 | 30 | 0.15 | 0.2 |
|  | DE3-6 | 9.7129 | 10.0397 | 0.3268 | 68 | 32 | 0.15 | 0.2 |
|  | DE3-8 | 9.7382 | 10.0255 | 0.2873 | 59 | 28 | 0.15 | 0.2 |
|  | DE3-9 | 9.6779 | 9.9704 | 0.2925 | 61 | 29 | 0.15 | 0.2 |
|  | DE3-10 | 9.7044 | 10.2559 | 0.5515 | 114 | 55 | 0.15 | 0.2 |
|  | DE3-13 | 9.7431 | 10.0625 | 0.3194 | 66 | 32 | 0.15 | 0.2 |
|  | DE4-1 | 9.7800 | 10.3318 | 0.5518 | 118 | 53 | 0.15 | 0.2 |
|  | DE4-2 | 9.7597 | 10.2092 | 0.4495 | 96 | 43 | 0.15 | 0.2 |
|  | DE4-3 | 9.7431 | 10.2975 | 0.5544 | 118 | 53 | 0.15 | 0.2 |
|  | DE4-4 | 9.9217 | 10.4568 | 0.5351 | 114 | 52 | 0.15 | 0.2 |
|  | DE4-5 | 9.8365 | 10.3395 | 0.5030 | 107 | 48 | 0.15 | 0.2 |
| 26 | D11-1 | 11.1081 | 11.6076 | 0.4995 | 125 |  | 0.15 | 0.2 |
|  | D11-2 | 11.0809 | 11.7628 | 0.6820 | 171 |  | 0.15 | 0.2 |
|  | D11-3 | 11.0574 | 11.5680 | 0.5106 | 128 |  | 0.15 | 0.2 |
|  | D12-9 | 10.7825 | 11.2481 | 0.4656 | 91 |  | 0.15 | 0.2 |
|  | D12-12 | 10.8994 | 11.2892 | 0.3898 | 62 |  | 0.15 | 0.2 |
|  | D12-13 | 10.7833 | 11.1219 | 0.3386 | 54 |  | 0.15 | 0.2 |
|  | D12-18 | 10.7453 | 11.0837 | 0.3384 | 54 |  | 0.15 | 0.2 |
|  | D12-19 | 10.9574 | 11.2847 | 0.3273 | 60 |  | 0.15 | 0.2 |
|  | D12-20 | 10.7963 | 11.1812 | 0.3849 | 71 |  | 0.15 | 0.2 |
|  | D12-27 | 10.7865 | 11.1805 | 0.3940 | 73 |  | 0.15 | 0.2 |
| 27 | DE9-1 | 8.0523 | 8.5517 | 0.4994 | 109 | 47 | 0.15 | 0.2 |
|  | DE9-2 | 7.9910 | 8.4420 | 0.4510 | 99 | 43 | 0.15 | 0.2 |
|  | DE9-3 | 8.0329 | 8.4513 | 0.4184 | 92 | 40 | 0.15 | 0.2 |
|  | DE9-4 | 8.0568 | 8.5276 | 0.4708 | 103 | 45 | 0.15 | 0.2 |
| 27 | DE9-5 | 7.9340 | 8.3550 | 0.4210 | 92 | 40 | 0.15 | 0.2 |
|  | DE9-7 | 8.1360 | 8.6043 | 0.4683 | 103 | 44 | 0.15 | 0.2 |
|  | DE9-8 | 8.0969 | 8.4299 | 0.3330 | 73 | 32 | 0.15 | 0.2 |
|  | DE9-9 | 8.0758 | 8.4074 | 0.3316 | 73 | 31 | 0.15 | 0.2 |
|  | DE9-10 | 8.0694 | 8.4250 | 0.3556 | 78 | 34 | 0.15 | 0.2 |
|  | DE9-11 | 8.0488 | 8.3668 | 0.3180 | 70 | 30 | 0.15 | 0.2 |

TABLE 3
Micrograms Levonorgestrel Released/Day

| Day | IVR No. 103 | IVR No. 104 |
|---|---|---|
| 1 | 849 | 918 |
| 2 | 507 | 411 |
| 3 | 449 | 488 |
| 4 | 583 | 488 |
| 5 | 611 | 541 |
| 8 | 608 | 486 |
| 9 | 506 | 515 |
| 10 | 635 | 497 |
| 11 | 617 | 460 |
| 15 | 626 | 506 |
| 16 | 635 | 580 |
| 17 | 690 | 607 |
| 18 | 820 | 591 |
| 22 | 696 | 611 |

TABLE 3-continued

Micrograms Levonorgestrel Released/Day

| Day | IVR No. 103 | IVR No. 104 |
|---|---|---|
| 23 | 658 | 534 |
| 24 | 643 | 643 |
| 25 | 614 | 586 |
| 29 | 614 | 558 |
| 30 | 558 | 548 |
| 31 | 591 | 563 |
| 32 | 596 | 572 |
| 36 | 668 | Lost |
| 37 | 591 | 448 |
| 43 | 592 | 532 |
| 44 | 612 | 552 |
| 45 | 582 | 632 |
| 50 | 700 | 623 |
| 51 | 690 | 652 |

TABLE 4

Micrograms Estradiol Released/day

| Day | IVR No. 103 | IVR No. 104 |
|---|---|---|
| 1 | 360 | 405 |
| 2 | 405 | 360 |
| 3 | 270 | 270 |
| 4 | 270 | 315 |

TABLE 5

Micrograms Levonorgestrel Released/day

| Day | IVR No. 101 | IVR No. 102 |
|---|---|---|
| 1 | 2509 | 2438 |
| 2 | 1874 | 1616 |
| 3 | 1931 | 1749 |
| 4 | 1874 | 1883 |
| 5 | 1567 | 1802 |
| 8 | 1731 | 1671 |
| 9 | 1730 | 1657 |
| 10 | 1660 | 1546 |
| 11 | 1666 | 1629 |
| 15 | 1381 | 1556 |
| 16 | 1510 | 1491 |
| 17 | 1721 | 1417 |
| 18 | 1574 | 1660 |
| 22 | 1469 | 1355 |
| 23 | 1460 | 1240 |
| 24 | 1370 | 1276 |
| 25 | 1380 | 1285 |
| 29 | 1304 | 1295 |
| 31 | 1250 | 1193 |
| 32 | 1383 | 1183 |
| 36 | 1107 | 1231 |
| 37 | 1116 | 1221 |
| 44 | 1274 | 1114 |
| 45 | 1114 | 1134 |
| 51 | 1050 | 987 |

TABLE 6

Micrograms Estradiol Released/day

| Day | IVR No. 101 | IVR No. 102 |
|---|---|---|
| 1 | 2600 | 2900 |
| 2 | 2600 | 2100 |
| 3 | 1800 | 1600 |
| 4 | 1400 | 1800 |

TABLE 7

Micrograms Levonorgestrol Released/day

| Day | IVR No. 108 | IVR No. 109 |
|---|---|---|
| 1 | 602 | 531 |
| 2 | 392 | 296 |
| 3 | 459 | 468 |
| 4 | 535 | 411 |
| 5 | 502 | 494 |

TABLE 7-continued

Micrograms Levonorgestrol Released/day

| Day | IVR No. 108 | IVR No. 109 |
|---|---|---|
| 8 | 506 | 479 |
| 9 | 598 | 543 |
| 10 | 598 | 479 |
| 11 | 589 | 515 |
| 15 | 561 | 571 |
| 16 | 571 | 442 |
| 17 | 525 | 525 |
| 18 | 630 | 563 |
| 22 | 592 | 506 |
| 23 | 515 | 515 |
| 24 | 520 | 501 |
| 25 | 529 | 491 |
| 29 | 595 | 501 |
| 30 | 501 | 454 |
| 31 | 572 | 544 |
| 32 | 439 | 506 |
| 36 | 477 | 477 |
| 37 | 487 | 458 |
| 38 | 477 | 477 |
| 43 | 432 | 442 |
| 44 | 371 | 472 |
| 45 | 492 | 482 |
| 50 | 527 | 566 |
| 51 | 431 | 498 |

TABLE 8

Micrograms Estradiol Released/day

| Day | IVR No. 108 | IVR No. 109 |
|---|---|---|
| 1 | 270 | 225 |
| 2 | 270 | 315 |
| 3 | 225 | 270 |
| 4 | 270 | 225 |

TABLE 9

Micrograms Levonorgestrel Released/day

| Day | IVR No. 110 | IVR No. 111 |
|---|---|---|
| 1 | 2782 | 2495 |
| 2 | 1969 | 1778 |
| 3 | 1960 | 1807 |
| 4 | 2017 | 1683 |
| 5 | 1724 | 1677 |
| 8 | 1580 | 1580 |
| 9 | 1604 | 1515 |
| 10 | 1614 | 1515 |
| 11 | 1643 | 1376 |
| 15 | 1417 | 1270 |
| 16 | 1436 | 1325 |
| 17 | Lost | 1086 |
| 18 | 1374 | 992 |
| 22 | 954 | 523 |
| 23 | 887 | 572 |
| 24 | 832 | 548 |
| 29 | 543 | 206 |
| 30 | 425 | 220 |
| 31 | 402 | Lost |
| 32 | 294 | 85 |
| 36 | 167 | 64 |
| 37 | 72 | Zero |
| 38 | 90 | |

TABLE 10

Micrograms Estradiol Released/day

| Day | IVR No. 110 | IVR No. 111 |
|---|---|---|
| 1 | 2400 | 2700 |
| 2 | 2400 | 2500 |
| 3 | 1800 | 1400 |
| 4 | 1300 | 1200 |

TABLE 11

| | Micrograms Levonorgestrel Released/Day | | | |
|---|---|---|---|---|
| Day | IVR No. 201 | IVR No. 203 | IVR No. 202 | IVR No. 205 |
| 1 | 2101 | 2059 | 466 | 373 |
| 2 | 2299 | 1826 | 454 | 297 |
| 3 | 1687 | 1678 | 343 | 454 |
| 4 | 1752 | 1594 | 389 | 482 |
| 8 | 1479 | 1526 | 448 | 401 |
| 9 | 1574 | 1507 | 448 | 410 |
| 15 | 1254 | 1435 | 381 | 442 |
| 16 | 1254 | 1284 | 462 | 492 |
| 17 | 1415 | 1335 | 582 | 482 |
| 18 | 959 | 1131 | 383 | 316 |
| 22 | 1045 | 1083 | 518 | 527 |
| 23 | 1035 | 1035 | 546 | 518 |

TABLE 12

| | Micrograms Estradiol Released/Day | | | |
|---|---|---|---|---|
| Day | IVR No. 201 | IVR No. 203 | IVR No. 202 | IVR No. 205 |
| 1 | 2300 | 2100 | 270 | 270 |
| 2 | 1600 | 1700 | 180 | 225 |
| 3 | 1300 | 1200 | 225 | lost |
| 4 | 1300 | 1200 | 180 | 180 |
| 8 | 760 | 760 | 180 | 225 |

TABLE 13

| | Micrograms Levonorgestrel Released/Day | |
|---|---|---|
| Day of Diffusion | IVR No. 213 | IVR No. 214 |
| 1 | 527 | 527 |
| 3 | 301 | 285 |
| 4 | 293 | 285 |
| 6 | 243 | 245 |
| 8 | 235 | 280 |
| 13 | 251 | 264 |
| 16 | 241 | 323 |
| 20 | 243 | 207 |

TABLE 14

| | Micrograms Levonorgestrel Released/day | | | |
|---|---|---|---|---|
| Day | H-70-1 | H-70-2 | H-70-5 | H-70-7 |
| 1 (After 5½ hrs) | 3080 | 3124 | 2496 | 3124 |
| 1 (After 24 hrs.) | 1811 | 1802 | 1466 | 1475 |
| 2 | 1134 | 1115 | 983 | 983 |
| 3 | 1011 | 1002 | 690 | 718 |
| 7 | 811 | 819 | 551 | 543 |
| 8 | 717 | 811 | 520 | 465 |
| 9 | 684 | 660 | 525 | 525 |
| 10 | 636 | 692 | 413 | 533 |
| 15 | 477 | 660 | 390 | 405 |
| 16 | 517 | 501 | 302 | 302 |
| 17 | 502 | 469 | 314 | 388 |
| 22 | 401 | 418 | 243 | 217 |
| 23 | 418 | 452 | 309 | 335 |
| 24 | | 426 | 410 | 251 | 301 |

TABLE 15

In vitro Tests for Four IVRS Used in Patents in Clinical Trials for Six Cycles

| | Micrograms Levonorgestrel Released/day | | | |
|---|---|---|---|---|
| Day | IVR No. 6 | IVR No. 8 | IVR No. 10 | IVR No. 14 |
| 1 | 1537 | 1214 | 1214 | 2265 |
| 2 | 983 | 649 | 501 | 686 |
| 3 | 547 | 510 | 510 | 640 |
| 4 | 528 | 464 | 454 | 501 |
| 9 | 496 | 429 | 467 | 515 |
| 16 | 478 | 391 | 430 | 596 |
| 17 | 498 | 430 | 576 | 488 |
| 18 | 488 | 430 | 547 | 488 |

Four IVRS Not Used in Clinical Trials

| | Micrograms Levonorgestrel Released/day | | | |
|---|---|---|---|---|
| Day | IVR No. 1 | IVR No. 2 | IVR No. 24 | IVR No. 38 |
| 1 | 1011 | 809 | 485 | 1456 |
| 2 | 732 | 795 | 797 | 565 |
| 3 | 649 | 584 | 695 | 640 |
| 4 | 612 | 538 | 501 | 473 |
| 9 | 591 | 477 | 477 | 448 |
| 16 | 664 | 508 | 459 | 518 |
| 17 | 557 | 625 | 605 | 410 |
| 18 | 586 | 469 | 527 | 420 |

TABLE 16

Breakthrough bleeding and Spotting among subjects using levonorgestrel contraceptive IVRs or levonorgestrel-estradiol contraceptive IVRs

| Type IVR | Number Subjects | Cycles with breakthrough bleeding or spotting/total cycles | Days with breakthrough bleeding and spotting/total days | Percent days with breakthrough bleeding or spotting |
|---|---|---|---|---|
| Levonorgestrel | 10 | 20/60 | 94/1250 | 7.52 |
| Levonorgestrel-Estradiol | 20 | 17/93 | 57/2063 | 2.77 |
| $X^2$ | | 3.72 not significant | 39.41 $p < 0.001$ | |

TABLE 17

STUDY DESIGN: PATIENT DISTRIBUTION (no. of women)

| TIME (months) | IVR | OVCON | ORTHO-N | NEOCON | Lo-OVRAL |
|---|---|---|---|---|---|
| 0 | 10 | 16 | 12 | 12 | 17 |
| 3 | 10 | 16 | 12 | 12 | 16 |
| 6 | 10 | 11 | 9 | 6 | 14 |
| 12 | | 6 | 4 | 2 | 3 |

TABLE 18

| | TRIGLYCERIDES-mg/100 ml | | | | |
|---|---|---|---|---|---|
| TIME (months) | IVR | OVCON | ORTHO-N | NEOCON | LO-OVRAL |
| 0 | 64 ± 28 | 80 ± 42 | 87 ± 44 | 70 ± 30 | 77 ± 30 |
| 3 | 43 ± 11* | 95 ± 30 | 115 ± 42 | 102 ± 26 | 84 ± 48 |
| 6 | 41 ± 15** | 105 ± 34 | 127 ± 47 | 117 ± 46 | 78 ± 26 |
| 12 | | 98 ± 26 | 177 ± 41 | 140 ± 57 | 75 ± 24 |

*IVR VS. ALL ORAL CONTRACEPTIVES P<0.001
**IVR VS. ALL ORAL CONTRACEPTIVES P<0.02

TABLE 19

ANGIOTENSINOGEN ng/ml

| TIME (months) | IVR | OVCON | ORTHO-N | NEOCON | LO-OVRAL |
|---|---|---|---|---|---|
| 0 | 907 ± 200 | 891 ± 351 | 996 ± 253 | 1260 ± 600 | 880 ± 259 |
| 3 | 936 ± 328* | 3377 ± 1040 | 4282 ± 1107 | 3240 ± 963 | 2736 ± 1092 |
| 6 | 840 ± 410* | 3733 ± 813 | 3617 ± 666 | 2160 ± 1867 | 2860 ± 959 |
| 12 |  | 3900 ± 764 | 3960 ± 318 |  |  |

*IVR VS. ALL ORAL CONTRACEPTIVES  $P<0.0005$

TABLE 20

CBG-BC - µg/100 ml

| TIME (months) | IVR | OVCON | ORTHO-N | NEOCON | LO-OVRAL |
|---|---|---|---|---|---|
| 0 | 14.16 ± 0.99 | 15.18 ± 2.36 | 15.14 ± 2.16 | 17.73 ± 3.88 | 16.97 ± 2.94 |
| 3 | 13.63 ± 1.25* | 38.40 ± 11.90 | 37.57 ± 6.94 | 39.88 ± 5.80 | 36.87 ± 9.47 |
| 6 | 15.27 ± 1.86* | 44.46 ± 9.45 | 38.27 ± 6.98 | 38.46 ± 12.72 | 37.95 ± 8.08 |
| 12 |  | 37.29 ± 12.58 | 37.8 ± 7.02 | 43.50 ± 2.09 | 37.10 ± 2.73 |

*IVR VS. ALL ORAL CONTRACEPTIVES  $P<0.005$

We claim:

1. A shell design intravaginal ring comprising in combination a core made of an inert elastomer, a medicated layer encircling the core, and an outer inert elastomer layer having a thickness of about 0.1 to 0.6 mm, the medicated layer comprising an inert elastomer and a combination of estradiol with a progestogen selected from the group consisting of levonorgestrel, d,l-norgestrel and norethindrone and the medicated layer having a thickness of not more than twice the thickness of the outer layer.

2. The intravaginal ring described in claim 1 wherein the progesten is levonorgestrel and the outer layer is about 0.2 mm thick.

3. The intravaginal ring described in claim 1 wherein the inert elastomer is a polysiloxane.

4. The intravaginal ring as described in claim 1 wherein the inert elastomer is a polysiloxane, the medicated layer contains about 70 mg levonorgestrel and about 35 mg estradiol and the outer layer is about 0.2 mm thick.

5. The intravaginal ring as described in claim 4 wherein the medicated layer contains about 40-240 mg levonorgestrel and about 30-100 mg estradiol.

6. A method of contraception which comprises the steps of retainably positioning within the vaginal tract an intravaginal ring as defined in claim 1.

7. A method of contraception, which comprises the steps of retainably positioning within the vaginal tract an intravaginal ring as defined in claim 1 retaining the ring in place for an approximate three week period, and removing the ring for an approximate one week period to permit menstruation.

8. A method of manufacturing a shell design intravaginal ring which consists of:
   (a) forming a core ring of a suitable inert elastomer;
   (b) dipping the core ring in a mixture of an inert volatile solvent containing an inert unvulcanized elastomer and a mixture of estradiol and a progestogen to form a medicated layer;
   (c) removing the ring from the mixture and allowing the solvent to evaporate;
   (d) repeating steps b and c until a medicated layer of the desired thickness is obtained;
   (e) dipping the ring from step d into a mixture of an inert unvulcanized elastomer in an inert volatile solvent removing the ring and allowing the solvent to evaporate to form an outer layer; and
   (f) repeating step e until an outer layer of desired thickness is obtained.

9. The method of manufacturing intravaginal rings as described in claim 1 wherein the progestogen is selected from the group consisting of levonorgestrel, d,l-norgestrel and norethindrone.

10. A method of manufacturing a shell design intravaginal ring which consists of:
    (a) forming an annular core ring of a suitable inert elastomer by injecting the unvulcanized elastomer into a mold and allowing the ring to cure in the mold;
    (b) removing the core ring from the mold and cutting the ring open;
    (c) bringing the open ring to a constant weight;
    (d) pulling the open ring through a coating solution containing an unvulcanized elastomer and a mixture of estradiol and a progestogen;
    (e) dipping the coated open ring in a catalyst solution and allowing the coating to polymerize;
    (f) swelling a piece of tubing in volatile organic solvent and fitting it over the open ring from step e and allowing the solvent to evaporate;
    (g) trimming the excess tubing from the ends of the open ring and applying a medical grade adhesive to the ends of the open ring and on the surface of the ring close to the open end;
    (h) placing a piece of swollen tubing over both ends of the open ring to reform the ring and holding the ends of the open ring together for a few minutes and curing the ring for about 24 hours.

11. The method of manufacturing intravaginal rings as described in claim 10 wherein the progestogen is selected from the group consisting of levonorgestrel, d,l-norgestrel and norethindrone.

12. A method of manufacturing a shell design intravaginal ring which consists of:
    (a) forming a core rod of suitable inert elastomer by injecting the unvulcanized elastomer into a mold and allowing it to cure:
    (b) removing the resulting core rod and cutting it into lengths about 15.5 cm;
    (c) bringing the rod to a constant weight;

(d) pulling the rod through a coating solution containing a mixture of an unvulcanized elastomer and a mixture of estradiol and a progestogen;

(e) dipping the coated rod in a catalyst solution and allowing the coating to polymerize;

(f) swelling a piece of tubing in a volatile organic solvent, and sliding it over the coated rod from step e and allowing the solvent to evaporate;

(g) trimming the excess tubing from the ends of the rod and applying a medical grade adhesive to the ends of the rod and to the surface of the rod close to the end;

(h) placing a second piece of swollen tubing over both ends of the rod to form a ring and holding the ends of the rod together for 24 hours until the adhesive has cured.

13. The method of manufacturing intravaginal rings as described in claim 12 wherein the progestogen is selected from the group consisting of levonorgestrel, d,l-norgestrel and norethindrone.

* * * * *